United States Patent [19]
Richardson et al.

[11] Patent Number: 5,118,464
[45] Date of Patent: Jun. 2, 1992

[54] METHOD OF ULTRASONIC INSPECTION OF MATERIALS THROUGH OPAQUE BARRIERS

[75] Inventors: David L. Richardson, Los Gatos; James C. S. Tung, San Jose; James H. Terhune, San Jose; Gerald A. Deaver, San Jose, all of Calif.

[73] Assignee: General Electric Company, San Jose, Calif.

[21] Appl. No.: 669,450

[22] Filed: Mar. 15, 1991

[51] Int. Cl.[5] .............................................. G21C 17/02
[52] U.S. Cl. .................................... 376/252; 376/245; 73/623; 73/622; 73/592
[58] Field of Search ............... 376/245, 252, 249, 291, 376/292; 23/592, 620, 622, 623, 627

[56] References Cited

U.S. PATENT DOCUMENTS

| | | | |
|---|---|---|---|
| 4,096,757 | 6/1978 | Ishii et al. | 73/621 |
| 4,160,229 | 7/1979 | McGough | 340/7 R |
| 4,391,143 | 7/1983 | Cook et al. | 73/623 |
| 4,565,088 | 1/1986 | Crambes | 73/61.1 R |
| 4,593,568 | 6/1986 | Telford et al. | 73/623 |
| 4,963,799 | 10/1990 | O'Loughlin | 315/345 |

Primary Examiner—Brooks H. Hunt
Assistant Examiner—Chrisman D. Carroll
Attorney, Agent, or Firm—Robert R. Schroeder

[57] ABSTRACT

An improved apparatus and method for ultrasonic inspection of materials through barriers such as gaps in manufactured parts is disclosed. The improvement herein is directed to enabling such ultrasonic testing to bridge ambient gaps such as intentionally formed gaps in composite structures having a first structure for originally receiving and transmitting sound separated by the gap from another structure to be inspected. Preferably, the gap is flooded with a gas having a predictable and optimum speed of sound relative to the material of the first and second structures. Sound is propagated to the first structure in a wave packet that is transmitted through the couplant fluid. The sound is generated in a wave packet having a spatial width at least twice the dimension of the gap to be bridged. The wave packet has a contained frequency having a wavelength (relative to the speed of sound of the gas flooding the gap) to create a constructively interfering standing wave node within the gap. The sound propagated to the gas-filled gap has a wavelength which is a half-integer with respect to the gap dimension. Sound passes through the first structure, creates a standing wave node in the gas-filled gap, passes into and acoustically interrogates the second structure for flaws and reflects. Reflected ultrasound from the interrogated second structure again bridges the gap as a constructively interfering standing wave, passing through the primary structure and then through the couplant fluid to a transducer for receipt and analysis of the received ultrasound.

16 Claims, 8 Drawing Sheets 0 dB 8.0 dB 44.0 dB 70.0 dB

METHOD OF ULTRASONIC INSPECTION OF MATERIALS THROUGH OPAQUE BARRIERS

This invention relates to nondestructive examination of material, such as metal, for voids, flaws, cracks, and the like that can be detrimental to the continuity and integrity of materials. More particularly, a method and apparatus for non-destructive examination is set forth in which the interrogating ultrasound bridges gaps—such as those gaps found between closely spaced manufactured parts. In the disclosure, sound is incident on a first material, bridges a manufactured gap to become incident upon a second material to be tested, is reflected at defects in the second material, returns across the manufactured gap, and is thereafter analyzed.

BACKGROUND OF THE INVENTION

Ultrasound has been used since the 1940's to nondestructively inspect a wide variety of materials for flaws, phase constitution, dimension measurement, grain structure and integrity. In particular, modern nondestructive examination (NDE) methods typically utilize sonic energy in the megahertz range to penetrate and image the inner body of metals, as well as their outer surfaces, taking advantage of their acoustical properties in locating discontinuities that reflect or scatter acoustical waves. The reflective property of voids, flaws, cracks, etc., that could be detrimental to the continuity and integrity of the material is the basis of NDE methodology. The frequency used is determined by the type of material and technique employed; for steel it is in the range of 1–10 megahertz with 2.25 to 5 megahertz the preferred range set by the propagation and attenuation characteristics of various steels. Other frequencies are used for zircaloy, titanium, aluminum and composite materials as dictated by their particular acoustic properties.

Typically, ultrasonic waves generated by a piezoelectric crystal transducer, common and known to the art, are introduced via a coupling fluid, such as water or acoustical grease, at the surface of the metal to be inspected. As the waves propagate in the bulk of the material they may impinge on some type of discontinuity affecting the acoustical impedance of the medium. It is well known in the science of acoustics that this impingement produces reflections and transmissions that compete against each other, depending on various factors such as flaw size and shape, angle of incidence, and magnitude of the change in impedance. In case of a gas gap (usually and naturally filled with air) change of impedance is so abrupt and large that virtually all of the incident sound waves are reflected at the interface. Very little sonic energy traverses such a gap, and inspection of material beyond an air gap is never considered in NDE practice. Thus, in many applications important to nuclear plant component inspections NDE effectiveness is limited by the presence of gaps that shield important joints and zones from inspection. An example is that of the control rod drive housing to stub-tube attachment weld and heat affected zone, known to be subject to cracking.

Referring to FIG. 1A, a reactor vessel V is shown in partial section to display a core C. Core C contains control rods, whose drive housings H extend through the bottom of the vessel V through stub-tubes T. Those familiar with the nuclear industry will recognize that FIG. 1A is a boiling water reactor operating under a standard pressure in the range of 1200 pounds. Further, the vessel is in the range of 120 feet in height, 30 feet in diameter, and contains radioactive material contained in fuel rods as the natural result of the nuclear reaction. The preferred nondestructive examination is directed at the stub-tube environment which is at the bottom head of vessel V.

Referring to FIG. 1B, bottom head 14 of the vessel V is illustrated at stub-tube T placed within a recessed aperture 15 of vessel V. Typically, the inside of vessel V can be clad with stainless steel 16. Connection of the stub-tube T to the cladding 16 and vessel V at bottom head 14 occurs at weld L. Similarly, connection of the control rod drive housing H occurs at the top of the stub-tube T.

It is required that the alignment of the control rod drive housing H within the stub-tube T be precise. Consequently, the stub-tube T and the control rod drive housing define a gap G therebetween. This gap G enables the verticality of the control rod drive housing H to be maintained during the placement of welds J.

Welds J and L, and the heat-affected zones adjacent to the welds are subject to certain conditions of metal cracking. Specifically, these zones have proven to be candidate zones for the metallic cracking defect known as intergranular stress corrosion cracking (IGSCC). Simply stated, the conditions of metallic tension, stagnation of water flow, and oxygen concentration cause crack propagation along the granular boundaries of the metal. This phenomenon is known to occur within and adjacent to welds L and J.

Before this disclosure, gap G prevented ultrasound examination of cracking in stub-tube T from the interior of control rod drive housing H.

SUMMARY OF THE PRIOR ART

The detection of gaps in the ultrasonic non-destructive examination of materials is known. See Applications of Ultrasonic Interference Spectroscopy to Materials and Flaw Characterization by B. G. Yee et al., "Materials Evaluation," August 1975. The detection of the gap has primarily been used either for measurement of the thickness of the materials, location of the faults in laminations, determining dimension of a gap, or other measurements all related to the gap itself. It has not been suggested by the prior art to examine utilizing ultrasound transmitted through and bridging the gaps to nondestructively test materials on the other side of gaps.

Gaps and their properties in transmitting and reflecting sound are understood. See J. and H. Krautkramer, "Ultrasonic Testing of Materials," 4th Edition, Springer-Verlag, New York 1990, pp. 18-23. Again, testing through the gaps to inspect materials on the other side of such gaps (see FIG. 1B at G) has not been set forth.

SUMMARY OF THE INVENTION

An improved apparatus and method for ultrasonic inspection of materials through barriers such as gaps in manufactured parts is disclosed. As in normal ultrasonic detection, a transducer sends a signal through a couplant fluid into the solid material to be inspected. Typically, a located discontinuity, such as a crack or other flaw, gives a reflecting echo. A transducer receives and transduces the reflected echo for electronic display of the acoustically reflected results. Analysis of the display and, hence, the time and character of echo received, results in nondestructive inspection and analysis for flaws and cracks. The improvement herein is directed to enabling such ultrasonic testing to bridge gaps, such as intentionally formed gaps in composite structures having a first structure for originally receiving and transmitting sound separated by the gap from another structure to be inspected. Preferably, the gap is flooded with a gas having a predictable and optimum speed of sound relative to the material of the first and second structures. Sound is propagated to the first structure in a wave packet that is transmitted through the couplant fluid. The sound is generated in a wave packet having a width at least twice the dimension of the gap to be bridged. The wave packet has a contained frequency having a wavelength (relative to the speed of sound of the gas flooding the gap) to create a constructively interfering standing wave within the gap. The sound propagated to the gas-filled gap has a standing wavelength, which is a half-integer with respect to the gap dimension. Sound passes through the first structure, creates a standing wave at the gas-filled gap, enters and acoustically interrogates the second structure for flaws and reflects. Reflected ultrasound from the interrogated second structure again bridges across the gap as a constructively interfering standing wave, passes through the primary structure and then through the couplant fluid to a transducer for detection and analysis of the received ultrasound. A disclosure of an analytic method coupled with the disclosed apparatus and process is made to enable analysis of a given geometry of gap, any given gas flooding the gap, any given interrogating wave packet, including the spectral power density and bandwidth, for bridging gaps having a given range of dimensions (usually 2 to 10 mils) between primary structures and nearby secondary structures to be interrogated, as well as other parameters that may be encountered in the use of the method. An example of a preferred inspection across the gap between a control rod drive housing for interrogation of a stub-tube structure within a nuclear reactor is disclosed.

BRIEF DESCRIPTION OF THE DRAWINGS

Other objects, features and advantages of this invention will become more apparent after referring to the following specification and drawings in which.

DESCRIPTION OF THE PREFERRED EMBODIMENTS

We have discovered that it is possible to create conditions in sizeable gaps, typically 2-10 mils across, such that a standing wave of the proper frequency can be excited in a judiciously chosen gas, or gas mixture. We apply this discovery to permit the nondestructive examination by ultrasound of a boiling water nuclear reactor at a stub-tube from a control rod drive housing through a gas gap to examine the integrity of the welds of the control rod drive housing to the stub-tube and to the heat-affected zones adjacent to those welds.

Figure 1A:
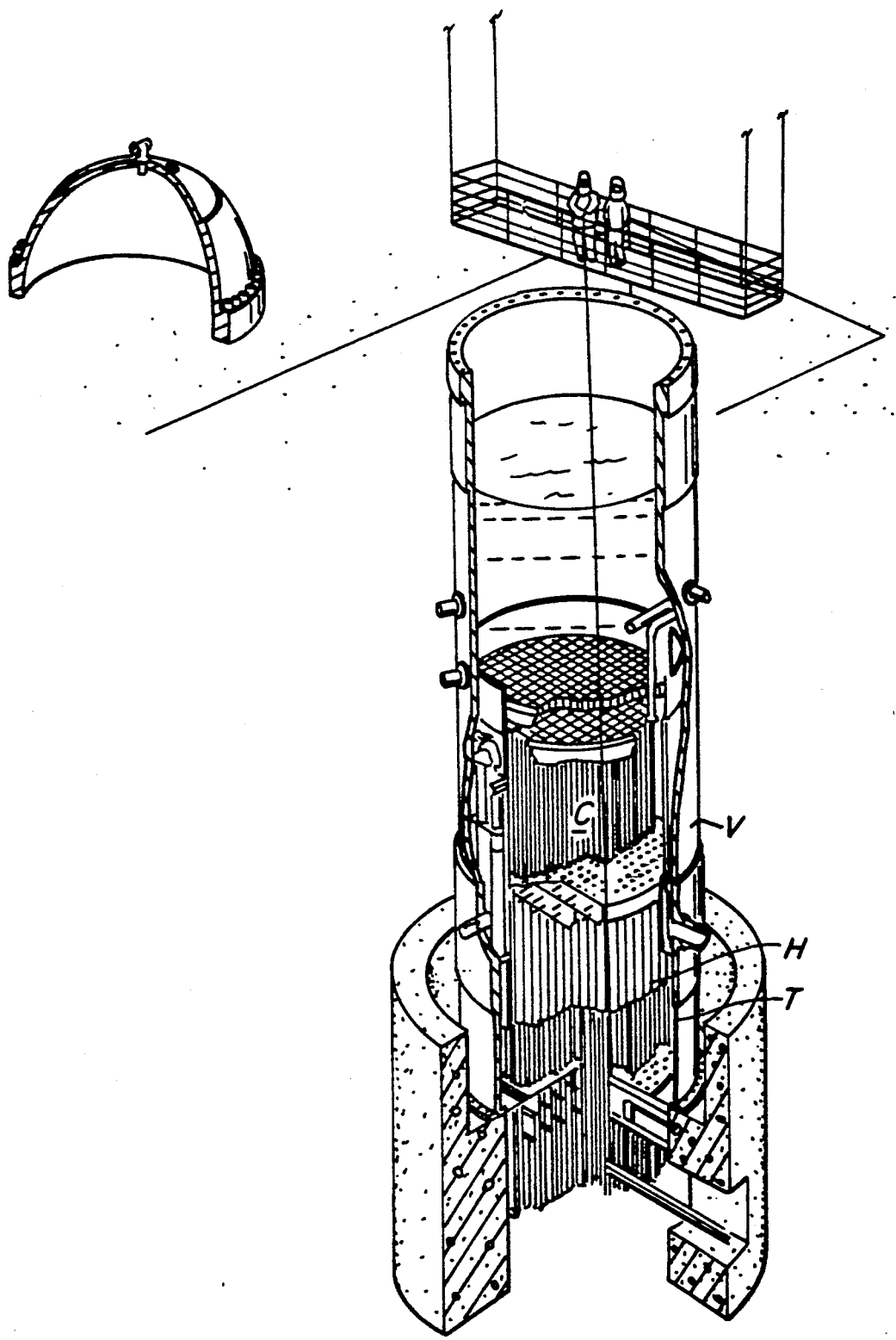
FIG. 1A is a schematic representation of a boiling water nuclear reactor illustrating the location of the site of the nondestructive testing of the preferred embodiment of this invention.
Figure 1B:
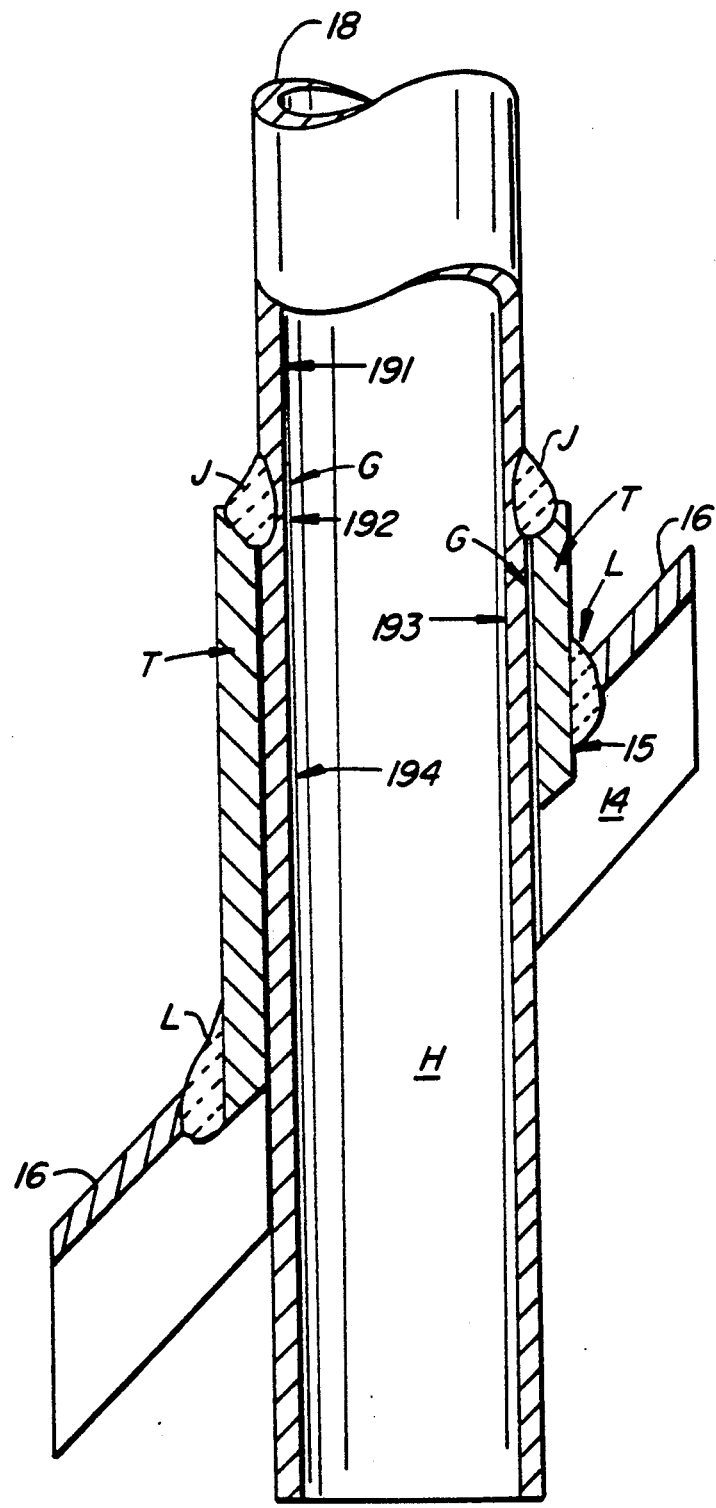
FIG. 1B is a detail of the boiling water reactor of FIG. 1A illustrating the construction of the bottom head of the reactor vessel at a typical stub-tube with the support of the control rod drive housing and core segment overlying the stub-tube.
Figure 1C:
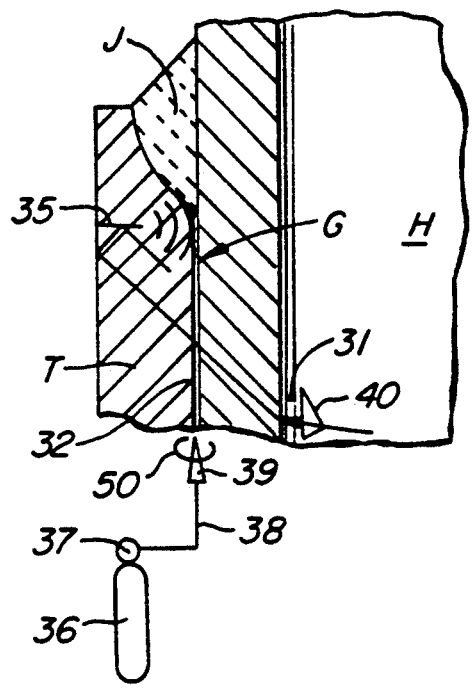
FIG. 1C is an expanded detail of FIG. 1B illustrating the gap between the control rod drive housing and stub-tube, it being the purpose of this invention to permit ultrasonic examination from the control rod drive housing, bridging of the gap to the stub-tube, with ultimate ultrasound nondestructive examination of the stub-tube at welds on the stub-tube and heat-affected zones of the stub-tube adjacent the welds.

With reference to FIG. 1C, it can be seen that a longitudinal acoustic wave from transducer 40 passes through couplant fluid 31 incident on the sidewall of control rod drive housing H. Thereafter, the ultrasound bridges narrow gap G containing a gas 32.

As will hereafter be understood, the wave when it is incident on an interface of gap G will be partially transmitted and partially reflected. This partial transmission and partial reflection will vary with the dimension of gap G, the medium in gap G and the frequency of the sound. Under the proper frequency of sound within medium 32, the partial transmission at one surface of gap G constructively interferes with the partial reflection at the opposite surface of gap G, creating a standing wave in the medium which fills the gap G. This effect occurs when the spatial extent of the standing wave exceeds the dimension of the gap, and the gap width is a half-integral number of wavelengths. The screening effect of the gas gap is thus defeated as a deterrent to NDE inspection of the medium behind it.

Referring further to FIG. 1C, wave incidence is shown within the metal to be interrogated at an angle of 45°. This enables the illustrated horizontal flaw to "corner trap" the reflected acoustical signal. This is standard nondestructive ultrasound inspection practice. The reader will understand that this is only one possible angle of incidence having utility. Other angles of incidence can be used.

To be effective a pulsed wave train of length larger than the gas gap must be excited, and either normal incidence or oblique incidence can be employed, depending on the frequency used. The theory is simplest for normal incidence of monochromatic sound yielding the following expression for the transmission coefficient at the interface between housing H and stub-tube T. The transmission coefficient T is:

$$T = 1/[1 + (\tfrac{1}{4})^*(r - 1/r)^2 \sin^2 2\pi d/\lambda] \qquad (1)$$

where:
$\lambda$ = sound wavelength
d = gap width
r = impedance ratio $Z_1/Z_2$

This formula shows that for arbitrary values of (d/$\lambda$) the transmission coefficient is dominated by the $(r - 1/r)^2$ term, when r is not unity. The resulting value of T is consequently very small, indicating a large reflection of energy at the gap interface. This is commonly the case for gas-filled gaps.

On the other hand, T is equal to unity from Eq. (1) when:

$$d/\lambda = n/2; \quad n = 1,2,3,\ldots \qquad (2)$$

indicating complete transmission of energy through the gap with no reflection whatever. Thus, if the gap dimension is any integral multiple of half-wavelength satisfying Eq. (2), transmission occurs.

It will be understood that gap G to this extent operates as a filter; reflected waves have the same wavelength. Therefore returning waves also are non-reflected, thereby allowing the scattered waves from a flaw to be detected by the transducer 40. It is clear that when Eq. (2) is satisfied, the impedance ratio, r, drops out of Eq. (1), and the propagation is independent of the impedance of the gas gap.

The ultrasonic frequency, f, is related to the wavelength by:

$$f = c/\lambda \qquad (3)$$

for linear media, such as steels and gases. To be useful the frequency should fall in a range for efficient propagation in metals (e.g., steel).

Combining Eqs. (2) and (3) yields:

$$f = nc/2d; \quad n = 1,2,3 \ldots \qquad (4)$$

where c is the speed of sound in the gas. Taking n = 1 for the moment, it is clear that a judicious choice of gas in the gap of width d allows f in the 2-5 megahertz range to be efficiently propagated in metals. When n is a larger integer, another mode is propagated as a standing wave in the gap, again allowing full transmission, a fact of use in larger gaps. To demonstrate the standing wave effect in various gases, Table 1 has been prepared. Helium, hydrogen, water and dry air are considered as examples, and similar results apply to other gases and mixtures.

TABLE 1

Gap Transmission Frequencies At Normal Incidence For Various Fluids

| Frequency (MHZ) | Gas/Liquid In Gap | Gap Width for T = 1 (mils) | | |
|---|---|---|---|---|
| | | N = 1 | N = 2 | N = 3 |
| 2.010 | He | 9.5 | 19.0 | 28.5 |
| 2.247 | He | 8.5 | 17.0 | 25.5 |
| 2.547 | He | 7.5 | 15.0 | 22.5 |
| 2.938 | He | 6.5 | 13.0 | 19.5 |
| 3.820 | He | 5.0 | 10.0 | 15.0 |
| 4.775 | He | 4.0 | 8.0 | 12.0 |
| 6.367 | He | 3.0 | 6.0 | 9.0 |
| 6.945 | He | 2.75 | 5.5 | 8.25 |
| 2.016 | $H_2$ | 12.5 | 25.0 | 37.5 |
| 2.800 | $H_2$ | 9.0 | 18.0 | 27.0 |
| 3.150 | $H_2$ | 8.0 | 16.0 | 24.0 |
| 3.600 | $H_2$ | 7.0 | 14.0 | 21.0 |
| 4.200 | $H_2$ | 6.0 | 12.0 | 18.0 |
| 5.040 | $H_2$ | 5.0 | 10.0 | 15.0 |
| 6.300 | $H_2$ | 4.0 | 8.0 | 12.0 |
| 6.720 | $H_2$ | 3.75 | 7.5 | 11.25 |
| 2.014 | Liq.$H_2O$ | 14.5 | 29.0 | 43.5 |
| 2.336 | Liq.$H_2O$ | 12.5 | 25.0 | 37.5 |
| 2.920 | Liq.$H_2O$ | 10.0 | 20.0 | 30.0 |
| 3.893 | Liq.$H_2O$ | 7.5 | 15.0 | 22.5 |
| 4.867 | Liq.$H_2O$ | 6.0 | 12.0 | 18.0 |
| 5.840 | Liq.$H_2O$ | 5.0 | 10.0 | 15.0 |
| 6.489 | Liq.$H_2O$ | 4.5 | 9.0 | 13.5 |
| 6.871 | Liq.$H_2O$ | 4.25 | 8.5 | 12.75 |
| 2.150 | Dry Air | 3.00 | 6.0 | 9.00 |
| 2.580 | Dry Air | 2.50 | 5.0 | 7.50 |
| 3.225 | Dry Air | 2.00 | 4.0 | 6.00 |
| 4.300 | Dry Air | 1.50 | 3.0 | 4.50 |
| 5.160 | Dry Air | 1.25 | 2.5 | 3.75 |
| 6.450 | Dry Air | 1.00 | 2.0 | 3.00 |
| 6.935 | Dry Air | 0.93 | 1.86 | 2.79 |

The objective of this invention is to utilize the implications of Eq. (4) in an embodiment conducive to NDE applications, especially in nuclear power plants, including appropriate means of introducing gases favorable to the propagation of sound in metals for the purpose of detecting anomalies ordinarily inaccessible to ultrasound. A second objective of the instant invention is to enhance the usefulness of ultrasonic inspections and extend the state-of-the-art in those applications heretofore considered inappropriate for NDE. Still a third objective is to provide a method and apparatus for detecting flaws in materials behind and obstructed by reflecting media, or gaps, thereby enhancing safety and reliability of the material component.

Figure 2:
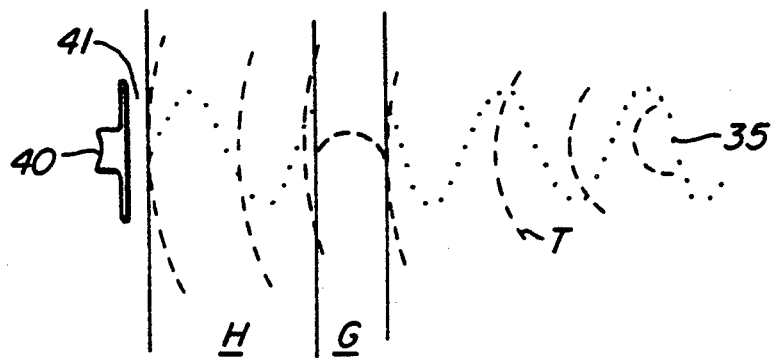
FIG. 2 is a schematic representation of normal ultrasound interrogation of two mediums, here stainless steel, separated by a manufactured gap to enable sound incident in one medium to be utilized in the ultrasound inspection of the second medium with the sound bridging the manufactured gap on both incidence and return from the examination.

The invention can further be described with reference to the schematic representation of FIG. 2. This wave path is normally incident to the surface being interrogated; the information received will be relevant to axially aligned defects. The reader will understand that initial access occurs from inside the control rod drive housing H. Control rod drive housing H and stub-tube T are joined by weld J (not shown), which has an axial flaw 35 in the heat-affected zone, which is inaccessible to direct inspection techniques from either the inner or outer tube surfaces. It will be understood that the function of the stub-tube T is to bridge the dissimilar metals and shapes between the vessel V and the control rod drive housing H.

By exciting the transducer 40, a longitudinal ultrasonic wave (L-wave) is coupled to the inner surface by couplant 41 (which is here, the normal water in the reactor). An L-wave is generated in the control rod drive housing H. At the correct frequency the wave bridges the gap G, and an L-wave is introduced into the stub-tube T, which is reflected at the outer tube surface and impinges on the flaw 35, where it is reflected. The return path of the reflected wave also bridges the gap, and the wave impinges on the transducer 40, where it is detected as a "pulse-echo" signal.

A complete understanding of the physics demonstrates that the dimension of the interrogating and reflected wave is important, as shown above. Specifically, a small period of time is required for the first incident wave at the correct frequency to traverse gap G. A portion of this wave is reflected and a portion of this wave is transmitted at the far boundary of the gap G. The wave reflected from the far boundary of the gap G constructively interferes with further incident sound waves of the correct frequency. This sets up the required standing wave for the transmission that we use that "bridges" the gap G. Although the creation of this condition is essentially in "real time", it is important to understand that the wave packet must have an adequate spatial dimension to create this standing wave. This must be at least twice the dimension of the gap for the medium contained within the gap.

By proper axial positioning of the transducer, a longitudinal tip-diffraction signal is generated, accompanied by a reduced pulse-echo signal. This signal is also detected by the transducer in a distinct time and amplitude relation to the pulse-echo signal. Analysis of these signals allows detection and sizing of the flaw, even though it is located behind what has been until now an "opaque" barrier (i.e., a gas-gap).

The reader will further appreciate that the disclosure does not use monochromatic sound - although most analysis for the reflection and transmission of ultrasound at such gaps has been theoretically determined for monochromatic waves. In fact, it may be necessary to "tune" the transducer 40 to receive the most beneficial signal. Such tuning is best done on the frequency of the normally incident waves such as those illustrated in FIG. 2.

Returning to FIG. 1C, and in order to facilitate ultrasonic wave propagation in relatively small gaps, helium gas 36 is injected under pressure into the annulus of gap G with flow controlled by regulator 37, gas line 38 and nozzle 39. The air originally in the gap is forced out by the excess helium pressure, and the lighter gas is maintained in the gap G by gravity after a short initial transient. Back diffusion of air is slow and is minimized by continued helium gas bled into the gap. Preferably, a collar 50 is utilized to plug the open bottom of the upwardly closed annulus which comprises gap G. This collar is schematically shown in FIG. 1C.

In the application of the boiling water reactor, it will be understood that the gap G between stub-tube T and control rod drive housing H will form an annular cavity. This annular cavity will be closed at the upper end by weld J. After long periods of reactor operation, this annulus will be filled with moist air - usually of unknown water content (or humidity). For this reason, the substitution of gases having known transmission features is desired.

It will be understood that the helium introduced under pressure displaces this moist air. Specifically, the light helium will move to the top of the annulus; air will be displaced to the bottom of the annulus. Further, it has been determined that any remaining moist air will have little effect. Further, once the displacement has occurred, diffusion will occur slowly in the narrow confines of gap G.

The speed of sound in helium at one atmosphere is about $0.382 \times 10^5$ in. per sec., whereas in air at one atmosphere, it is $0.129 \times 10^5$ in. per sec at 0% relative humidity. In many applications relative humidity is a strong variable, which is also eliminated by the introduction of the helium in displacing of the gas.

For oblique incidence with $n=1$, and a nominal gap width of 0.007 in., excellent transmission occurs at a frequency very nearly 2.7 megahertz, well within the preferred frequency window. On the other hand, dry air would require roughly 1.3 megahertz, which is outside the preferred range and subject to significant variability due to uncontrolled water vapor content.

The calculations utilized pertain to stainless steel for materials of the control rod drive housing H and the stub-tube T; similar calculations lead to favorable results for other metals.

Experimentally, the validity of Eq. (4) was checked by a transmission measurement at normal incidence through the tube walls H and T across the gap G in a model. With only air in the gap G, the transmission was observed to be very poor using peak spectral frequencies of 2.25 and 5 megahertz. With helium injection excellent transmission was achieved at both frequencies for a nominal 0.007 in. gap. The ratio was not exactly 2, as expected, because the gap was slightly non-uniform. Eq. (4) is not exact for oblique incidence, so the proper frequency was determined empirically.

Transverse (shear) waves may also be used, although with different propagation paths between the transducer and suspected flaws. Used in conjunction with gap transmission, shear-waves of the proper frequency can enhance the observation of flaws in positions difficult to access directly. Shear-waves, per se, cannot exist in the gas gap, but they are mode-converted from oblique incidence of longitudinal waves at the metal surface and propagate in the metal with lower velocity than longitudinal waves. In some cases detection is more sensitive using shear-waves, because of their lower propagation velocity.

According to Eq. (3), for fixed frequency, the wavelength is proportional to sonic velocity. The lower velocity shear waves result in shorter wavelength and, consequently, improved resolution, if they are efficiently propagated in the metal.

For various gap sizes other gases and liquids are useful. For example, hydrogen gas has a longitudinal wave velocity of $0.504 \times 10^5$ in. per sec, and water has a value of $0.584 \times 10^5$ in. per sec. Clearly, Eq. (4) can be satisfied by a large number of combinations of n, d and c for various fluids in the gap. These combinations with associated modeconversions are also incorporated into this disclosure as diverse embodiments of the novel concept. This is illustrated for normally incident waves in Table 1 for pure fluids and for a helium/air/water mixture in Table 2.

TABLE 2

| GAP TRANSMISSION FREQUENCIES AT NORMAL INCIDENCE FOR .8/.16/.04 He/Air/Water Mixture | | | | |
|---|---|---|---|---|
| Frequency (MHZ) | Gap Width for T = 1 (mils) | | | |
| | N = 1 | N = 2 | N = 3 | N = 4 |
| 2.048 | 8.5 | 17.0 | 25.5 | 34.0 |
| 2.1766 | 8.5 | 16.0 | 24.0 | 32.0 |
| 2.487 | 7.0 | 14.0 | 21.0 | 28.0 |
| 2.902 | 6.0 | 12.0 | 18.0 | 24.0 |
| 3.482 | 5.0 | 10.0 | 15.0 | 20.0 |
| 4.352 | 4.0 | 8.0 | 12.0 | 16.0 |
| 5.803 | 3.0 | 6.0 | 9.0 | 12.0 |

TABLE 2-continued

GAP TRANSMISSION FREQUENCIES AT NORMAL
INCIDENCE FOR .8/.16/.04 He/Air/Water Mixture

| Frequency (MHZ) | Gap Width for T = 1 (mils) | | | |
|---|---|---|---|---|
| | N = 1 | N = 2 | N = 3 | N = 4 |
| 6.964 | 2.25 | 5.0 | 7.5 | 10.0 |

NOTE:
For 12 mil gap f = 2.902, or 4.352, or 5.803 are equally acceptable. A choice can be made to minimize attenuation in the metal, or to match existing transducers. Similar considerations apply to other frequencies.

Hydrogen can be either a fire or explosion hazard. Therefore, the use of helium is preferred.

It will be appreciated that in the environment set forth here, the exact dimension of gap G can never be precisely known. Specifically, tolerance of the gap G in the environment here illustrated can vary from metal to metal contact to about 15 mils. This being the case, tuning variation of the wave packet carrier (or central) frequency will be required until an acoustical signal having the proper characteristics for the zone to be inspected is achieved. Fortunately, such tuning can rapidly occur.

The reader will understand that we have illustrated a radial crack. Cracks may possess numerous orientations. Therefore, it will be seen that the transducers illustrated in FIGS. 3A and 3B hereafter also produce waves which have varying angles of incidence. This enables inspection of cracks of any angularity.

Figure 3A:
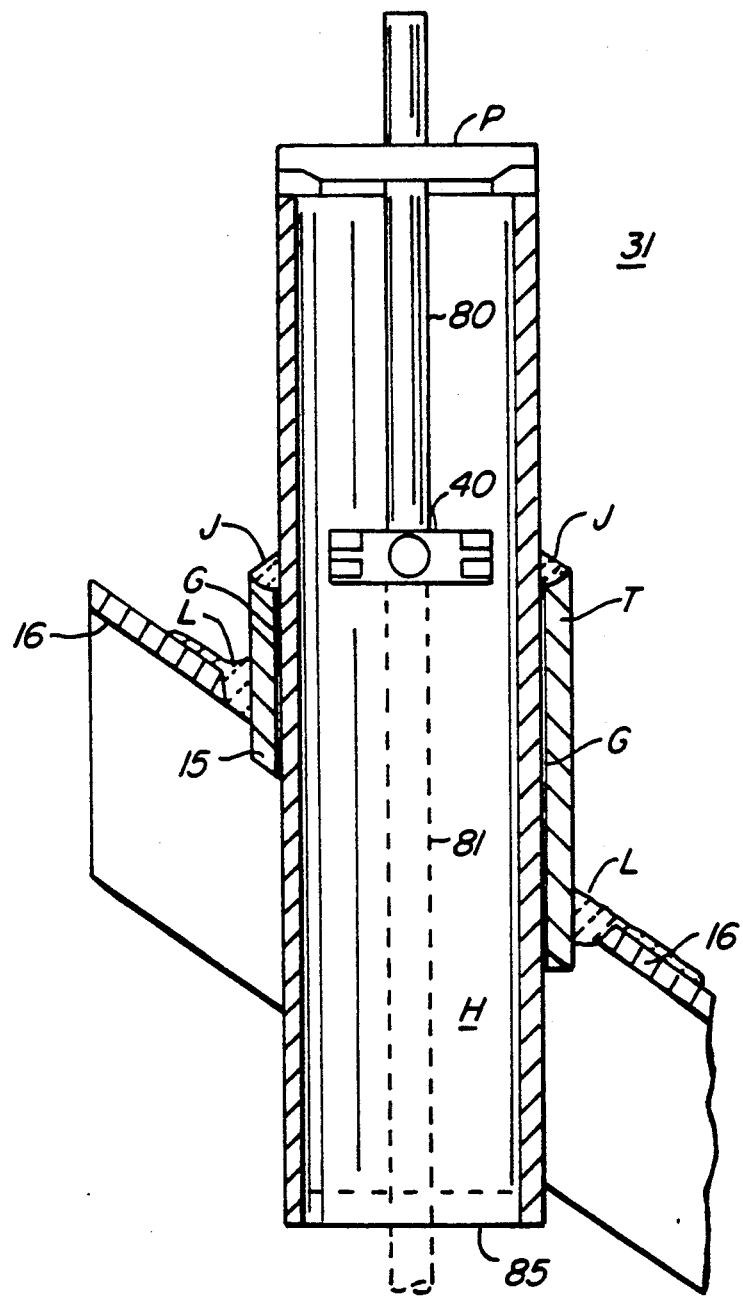
FIG. 3A is a side elevation taken at a control rod drive housing of a typical ultrasound probe custom constructed for the examination of a stub-tube, the illustration showing manipulation from the top of the reactor vessel in solid lines with alternative manipulation from below the reactor shown in broken lines.

Referring to FIG. 3A, an acoustical inspection utilizing the technique of this invention is shown underway. A circular acoustical head 40 is shown manipulated by a shaft 80 through a centering piece P on the top of a control rod drive housing H. Typically, such manipulation occurs from the top of the refueling bridge (not shown) when the reactor undergoes an outage. Alternatively, inspection can occur from below utilizing a seal 85 and a shaft 81; in this latter case entry will be made from below the reactor vessel V (See FIG. 1A).

As is well known, utilizing the water moderator surrounding the reactor as the couplant fluid, acoustical signals for interrogating the integrity of the control rod drive housing H occur.

Figure 3B:
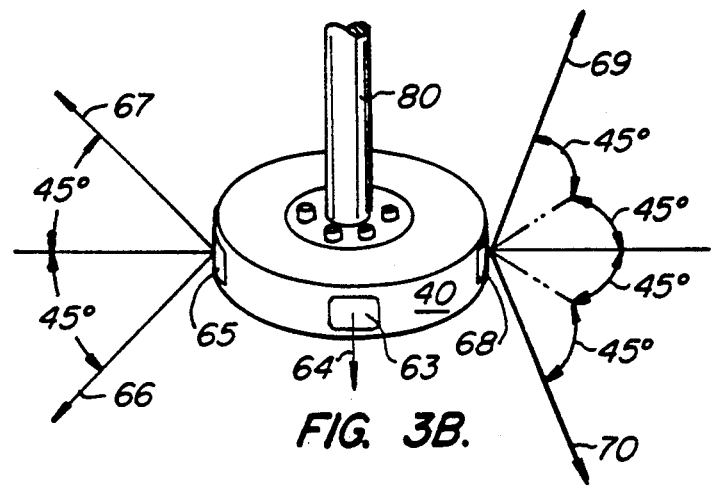
FIG. 3B is a perspective view of the probe of FIG. 3A illustrating with appropriate arrows the directions of sonic interrogation in the adjacent control rod drive housing and stub-tube.

Referring to FIG. 3B, the direction of interrogation within the control rod drive housing H and the stub-tube T is illustrated. The reader will understand that the direction of the acoustical interrogations shown are schematic to the interrogation of the steel only; it will be understood that the refraction that occurs from the water couplant fluid to the steel in accordance with Snell's Law is not shown in the perspective of FIG. 3B.

Referring to FIG. 3B, a first transducer 63 makes interrogation normally to the side walls of the control rod drive housing H and the stub-tube T. This interrogation being schematically shown at 64. Second transducer 65 makes interrogation at two 45° angles in a plane including the axis of shaft 80 and the radius of the acoustical housing 40 at transducer 65. Described from the plane of the acoustical housing 40, acoustical interrogation occurs 45° upwardly at vector 67 and 45° downward at vector 66. Finally, transducer 68 interrogates in what may be characterized as an upward counterclockwise vector 69 and a downward clockwise vector 70. Utilizing the acoustical examination of vector 67, it will be seen that vector 69 is rotated 45° counterclockwise; utilizing the acoustical examination of vector 66, it will be seen that vector 70 is rotated 45° clockwise.

Figure 4:
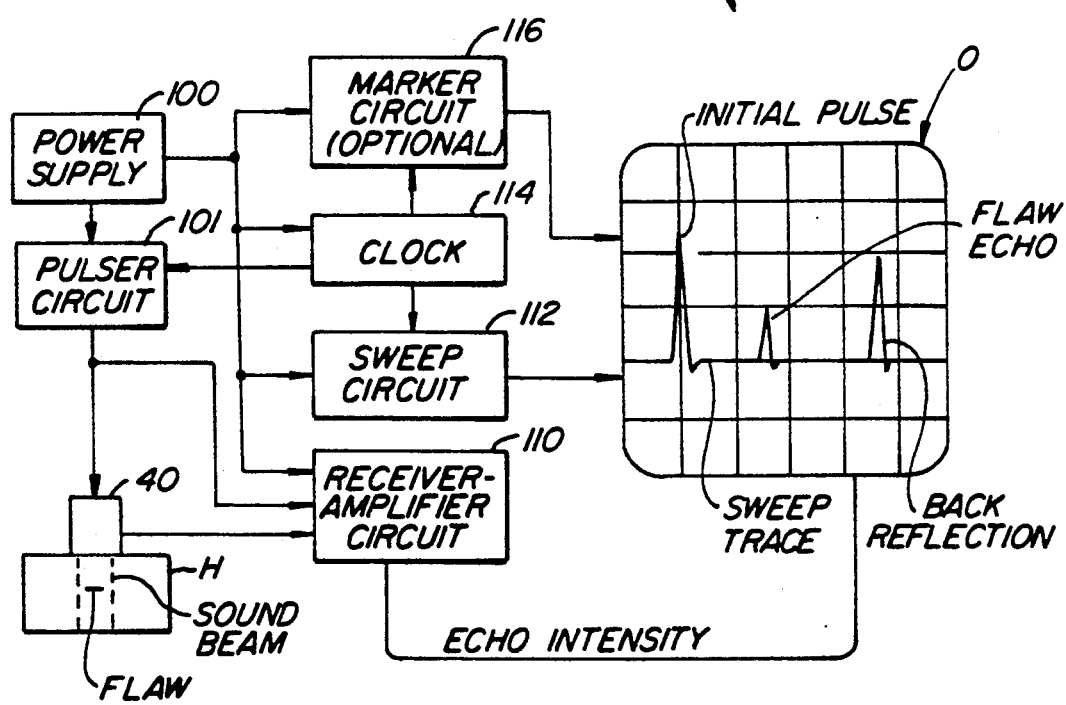
FIG. 4 is a schematic diagram of standard acoustical wave nondestructive testing apparatus.

Referring to FIG. 4, a prior art schematic of acoustical testing apparatus suitable for use with this invention is illustrated. A power supply 100 outputs to a pulser circuit 101 which transmits to the transducers 63, 65, or 68 (not shown) in transducer head 40. Returned sound is received at receiver-amplifier circuit 110 and displayed at oscilloscope O. As is conventional, clock 114 outputs to sweep circuit 112 with marker circuit 116 being utilized for the precise measurement of the displayed pulses.

Figure 5A:
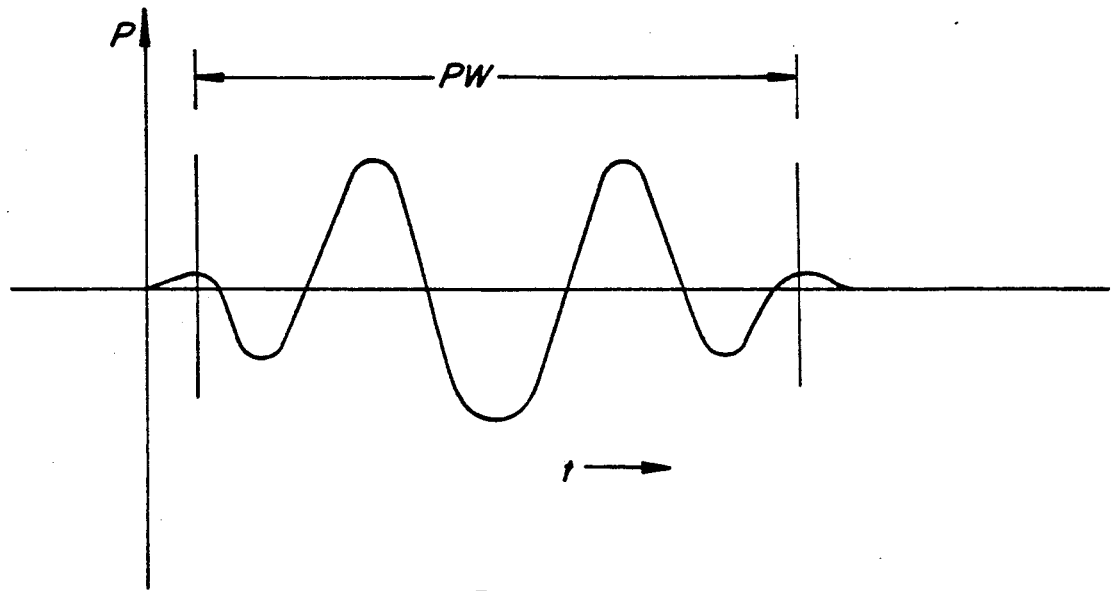
FIG. 5A is a diagram setting forth a plot of power versus time to illustrate the pulse width of a wave packet emitted from one of the acoustical transducers of FIG. 3B.

Referring to FIG. 5A, a plot of a typical acoustical signal with respect to time t is shown. The pulse width PW is labeled. It is to be understood that this pulse width PW, with respect to the speed of sound in gap G, has a dimension that is at least twice with width of the gap G. This enables the required standing wave to occur.

Figure 5B:
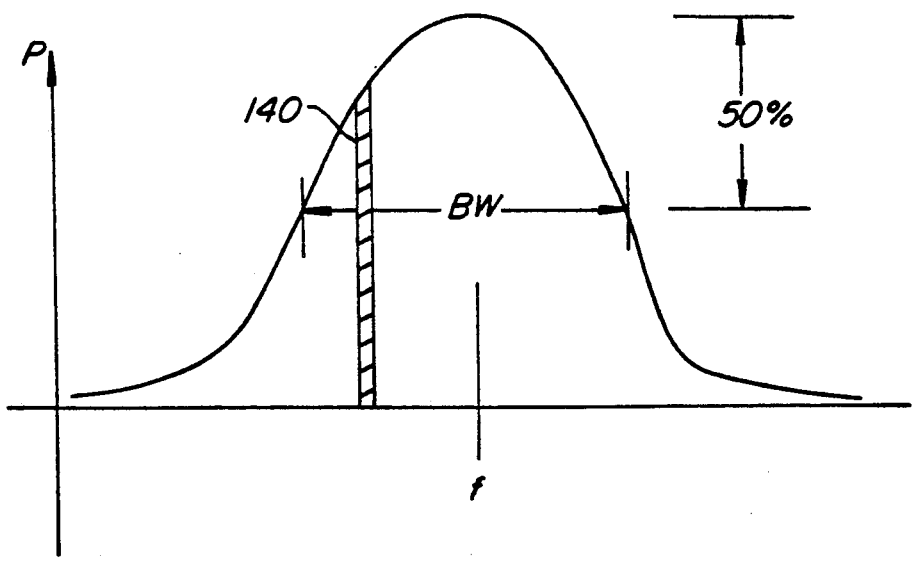
FIG. 5B is a diagram of the power spectral density of a pulse such as that illustrated in FIG. 5A illustrating the band width of the signal so that the reader can understand the frequency domain available for impingement upon a typical gap.

Referring to FIG. 5B, the so-called power spectral density of a Gaussian wave form is illustrated. Specifically, the wave form here has a "bell shaped" curve and is centered on an arbitrary frequency f (See Table 2); other wave forms characteristic of various transducers at varied power spectrums can be used. Frequencies in the illustrated wave packet exist on either side of the median frequency f, it being noted that the width of the packet at the 50% power range is referred to as the bandwidth BW.

Looking further at FIG. 5B, we have labeled a small portion of the frequencies at 140. These frequencies are exemplary of that small portion of frequencies that will be transmitted through a gap G of a given dimension. This partial transmission will occur because only that portion of the frequencies that is a half-integer multiple of the gap G dimension will be transmitted across the gap G. It will thus be understood that gap G acts as a filter; it only permits a small fraction of the originally transmitted wave to effect the interrogating penetration.

Figure 6A:
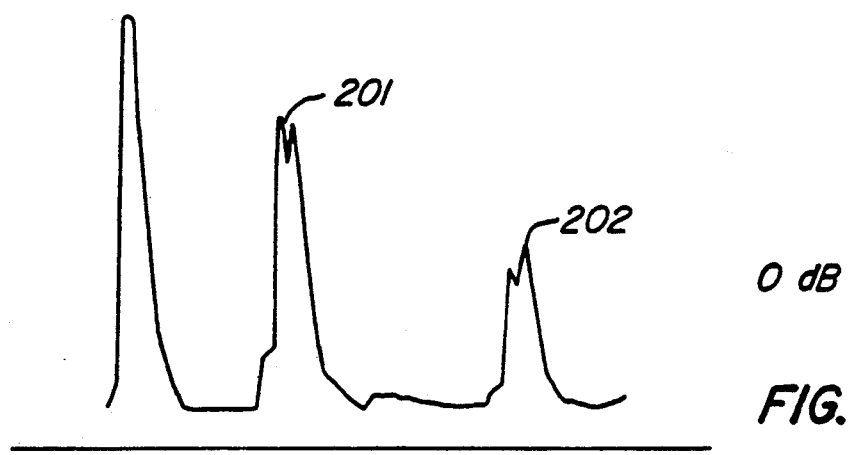
FIGS. 6A through 6D are sweep traces taken on an oscilloscope illustrating the nondestructive acoustical examination of this invention occurring at various identified locations illustrated with respect to FIG. 1B.

This effect may now be illustrated. Referring to FIG. 6A, a graphic representation of an oscilloscope plot is shown.

The plot of FIG. 6A is an acoustical interrogation taken normally to the control rod drive housing H and the stub-tube T. Zero db (decibels) gain has been utilized. The interrogation has occurred at 0° incidence. Wavelengths of 2.5 and 5 Mhz (megaHertz) have been used.

The interrogation occurs at location 191 from the control rod drive housing H. Only the control rod drive housing H is interrogated; no part of the stub-tube T is examined (see FIG. 1B). The plot shows the initial pulse followed by multiple reflections from the back wall at 201, 202. It will be understood that the full spectrum transmitted can, in effect, be returned. As is conventional, measurement of wall thickness is proportional to the time difference of the peaks of the illustrated plot of FIG. 6A.

Figure 6B:
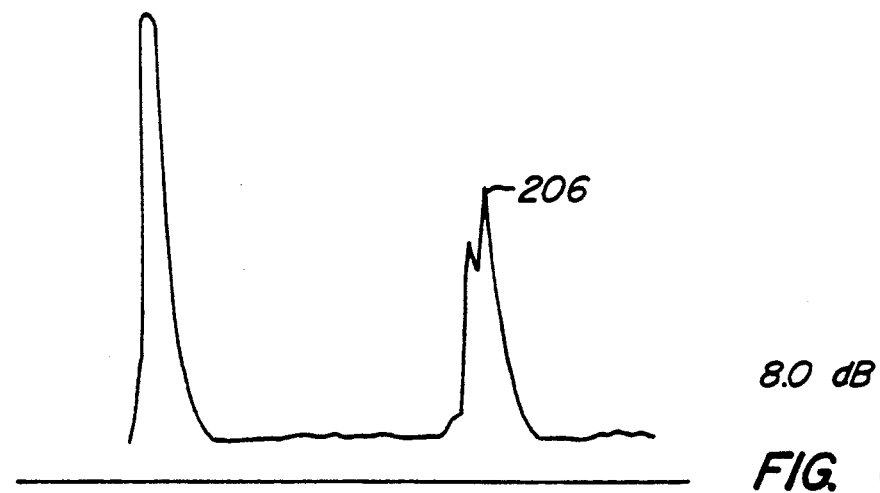

Referring to FIG. 6B, interrogation at weld J is illustrated at 192. Such interrogation occurs through the control rod drive housing H, the weld at J, and the stub-tube. An 8 db receiver gain was utilized. Here we see no back wall reflection from the control rod drive housing H. Displacement is larger because thickness has increased through the control rod drive housing and stub-tube as well as the mutually penetrating weld J.

The illustrated peak 206 occurs from the boundary of the stub-tube T.

Interrogation at 193 is exemplary of the invention herein. The plot of this penetration is similar to FIG. 6B except that transmission is through the gap. As set forth in the plot of FIG. 6C, considerable attenuation of the wave packet has occurred. Consequently, the receiver has a 44 db gain. There are considerable losses due to the fact that the transmitted waves across gap G only permit a small part of the energy to get through gap G (with 36 db loss).

Figure 6C:
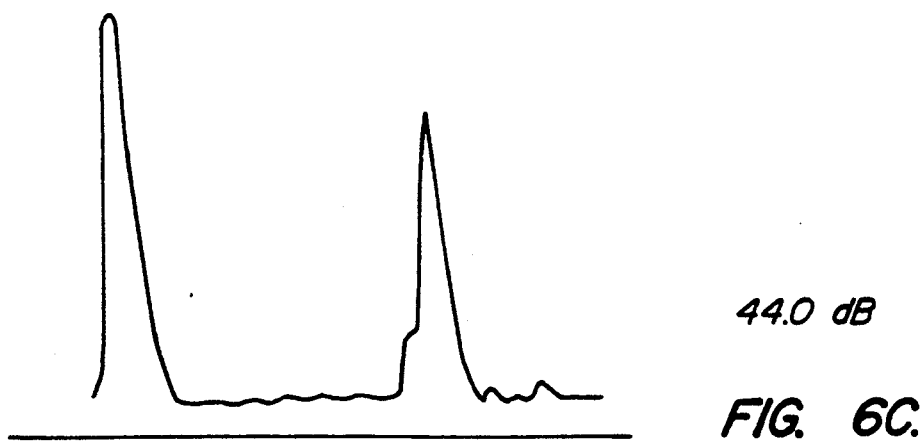

It will be understood that the time sequence of the pulses of FIG. 6B is identical to FIG. 6C. Helium in the gap G is transparent, only the gain is different. This difference in gain is the reflection of the energy at gap G that is off resonance.

Figure 6D:

In the experimental data shown at FIG. 6D, an interrogation was taken at 194. This portion of gap G was believed not to contain helium. Practically no energy was transmitted through the gap G. This plot is illustrated at a gain of 70 db.

An actual defect has been found using this technique. This has been done with the 45° incidence shown in FIG. 3B. The defect found constituted machine grooves on the outside of the stub-tube T, an area that was not accessible to ultrasound interrogation of the prior art. It is to be noted that such grooves are analogous to actual crack propagation. Cracks typically propagate from the outside of the stub-tube to and toward the control rod drive housing in the area adjacent to the weld.

We have found that size measurement of the detected cracks is also possible. Specifically, the tip of the crack when excited acoustically emanates diffracted acoustical signals. These diffraction signals contain information from which the dimension of the crack can be determined. Diffracted waves also penetrate the gas gap since their frequency is unchanged by the diffraction process. While size measurement is possible, that subject cannot be fully developed here at this time.

The consideration of a special case is relevant. Specifically, it may be possible for a crack to penetrate to gap G. In such penetration, gap G will become flooded with helium. It could possibly be that such a gap G could transmit sound rather than reflect sound if it happened to have a proper width. Such a gap G would be transparent to the non-destructive test in the highly unlikely circumstances cited.

In actual practice, it is believed that such a condition will not occur to a statistically significant degree. Cracks from intergranular stress corrosion cracking are irregular and of extremely small width compared to gap G—which is always a manufactured gap G. Such small-dimension irregular cracks will have a very high reflectance to the wavelengths disclosed here.

It will be understood that the stub-tube T and control rod drive housing example here illustrated is exemplary. The technique here disclosed will extend far beyond this limited environment.

Upon analysis, it will be understood that the substance used for filling the gap can be virtually any material. For example, it does not have to be a gas. Water, liquid sodium, or even a plastic could be utilized. Further, all types of normally tested solids may be utilized in some form.

The reader will further understand that the signal from a conventional pulsed transducer will have various power spectral densities and bandwidths, these being selected to provide the optimum result. Normally, before an inspection task is undertaken, analysis of the power spectral density and bandwidth against the speed of the ultrasound in the different media through which the sound passes will have to be examined. We disclose the following equations for use in the solution of this problem.

| PULSE WAVEFORM, POWER SPECTRAL DENSITY AND FOURIER TRANSFORM | |
|---|---|
| Exemplary Values | |
| $c = .97$ | where c is the sonic velocity in He gas gap (mm/μsec) |
| $n = .25$ | where $n < 1$ is the index of refraction relative to steel for longitudinal waves in the gas |
| $\theta = \frac{\pi}{4}$ | where $\theta$ is the angle of incidence at the steel-gas interface in the steel (rad) |
| $d = .002 \cdot 25.4$ | where d is the gas gap width (mm) |
| $m = 1$ | where m is the order of interference (1, 2, 3, 4 ...) |
| $V1 = .8$ | where V1, V2 are the volume fractions of He and air, respectively, in gap |
| $V2 = .2$ | |
| $c' = m \cdot c \cdot \sqrt{(v1 + .11775 \cdot V2)}$ | where c' is an effective sonic velocity for the mixture |
| $d' = \dfrac{d}{\sqrt{1 - (n \cdot \sin(\theta))^2}}$ | where d' is the effective width of the gap for obligue waves |
| $a = \dfrac{c'}{d'} \cdot \dfrac{\sqrt{\pi}}{8}$ | where a is the pulse attenuation coefficient |
| $b = \dfrac{c'}{d'} \cdot \pi$ | where b is the effective radian frequency |
| $BW = \dfrac{a}{\sqrt{\pi}}$ | where BW is the pulse bandwidth (MHz) |
| $PW = 1/BW$ | where PW is the effective pulse width (μsec) |

-continued

PULSE WAVEFORM, POWER SPECTRAL DENSITY AND FOURIER TRANSFORM

Exemplary Values $h_i = [a\ t]^2 \cdot e^{-[a \cdot t]^2} \cos[b \cdot t]$ where h is the pulse waveform (normalized)

$f = \dfrac{b}{2 \cdot \pi}$ where f is the nominal wave frequency (MHz)

$f1 = \left[ f + \dfrac{BW}{2} \right]$ where f1 is upper break frequency (MHz)

$f2 = \left[ f - \dfrac{BW}{2} \right]$ where f2 is lower break frequency (MHz)

$G = FFT[h(t)]$ where G is the normalized fast Fourier transfer of h
$PSD = |G|^2$ where PSD is the normalized power spectral density for the pulse It will be left to those having skill in the art to effect analysis utilizing the disclosed equations for selecting appropriate wave packets from the ultrasound technique here disclosed.

What is claimed is:

1. In a method of nondestructive acoustical inspection for discontinuities in solid structures including sending an ultrasound wave packet into a solid structure to be inspected, reflecting said ultrasound wave packet from a located discontinuity in the solid structure to be inspected, receiving and transducing the reflected echo of said ultrasound wave packet, and analyzing the reflected echo of said ultrasound wave packet for nondestructive interrogation of the solid structure inspected, the improved method for ultrasound inspection of solid structures through barriers in said solid structures, such as gaps in manufactured solid structures comprising the steps of:

providing a first solid structure for originally receiving said interrogating ultrasound;

providing a second solid structure separated from said first solid structure by a gap;

flooding said gap between said first and second solid structures with a medium, said medium having a predictable speed of ultrasound transmission for said wave packet;

transmitting an interrogating wave packet of ultrasound to said first solid structure, the ultrasound of said wave packet when traveling through media such as that media flooding said gap including an instantaneous standing path length within the media which is at least twice the dimension of the gap to be bridged, said interrogating wave packet of said ultrasound containing a frequency having a wavelength relative to the media in said gap to create at least one constructively interfering standing wave node between said first structure and said second solid structure within said media flooding said gap, whereby ultrasound of said frequency passes across said gap;

passing said ultrasound of said frequency into said second solid structure to acoustically interrogate said second solid structure for discontinuities through reflected ultrasound of said frequency;

providing a receiving transducer for receiving said reflected ultrasound of said frequency;

receiving said reflected ultrasound of said frequency at said receiving transducer from the interrogated second solid structure along a path including said second solid structure, said media flooding said gap at a constructively interfering standing wave, and said first solid structure for receipt and analysis of the received reflected ultrasound.

2. The method of claim 1 and wherein said medium flooding said gap is a gas.

3. The method of claim 2 and wherein said gas is an inert gas.

4. The method of claim 2 and wherein said gas is helium.

5. The method of claim 1 and wherein said interrogating ultrasound is normally incident on said first solid structure.

6. The method of claim 1 and wherein said provided solid structures are steel.

7. In a method of nondestructive acoustical inspection for discontinuities in solid structures including sending an ultrasound wave packet into a solid structure to be inspected, reflecting said ultrasound wave packet from a located discontinuity in the solid structure to be inspected, receiving and transducing the reflected echo of said ultrasound wave packet, and analyzing the reflected echo of said ultrasound wave packet for nondestructive interrogation of the solid structure inspected, the improved method for ultrasound inspection of solid structures through barriers in said solid structures, such as gaps in manufactured solid structures wherein an acoustical interrogating path must pass through a first solid structure, across said gap to interrogate a secondary solid structure for said discontinuity, the inspection process comprising the steps of:

flooding said gap between said first and second solid structures with a gas, said gas having a predictable speed of ultrasound transmission for said wave packet;

transmitting an interrogating wave packet of ultrasound to said first solid structure, the ultrasound of said wave packet when traveling through gas such as that gas flooding said gap including an instantaneous standing path length within the gas which is at least twice the dimension of said gap to be bridged, said interrogating wave packet of said ultrasound containing a frequency having a wavelength relative to the gas in said gap to create at least one constructively interfering standing wave node between said first solid structure and said second solid structure within said gas flooding said gap, whereby ultrasound of said frequency passes across said gap;

passing said ultrasound of said frequency into said second solid structure to acoustically interrogate said second solid structure for discontinuities through reflected ultrasound of said frequency;

providing a receiving transducer for receiving said reflected ultrasound of said frequency;

receiving said reflected ultrasound of said frequency at said receiving transducer from the interrogated second solid structure along a path including said second solid structure, said gas flooding said gap at a constructively interfering standing wave, and said first solid structure for receipt and analysis of the received reflected ultrasound.

8. The process of claim 7 and wherein said transmitting step includes transmitting differing frequencies to locate those frequencies producing an optimum standing wave node in said gap.

9. The process of claim 7 and wherein said providing said gas in said gap includes the step of:

displacing ambient gas in said gap with said flooded gas.

10. The process of claim 9 and wherein said flooded gas is helium.

11. The improved method for ultrasonic inspection of materials for flaws through barriers such as gaps between solid manufactured parts wherein interrogating ultrasound wave packets pass through a primary material, across said gap to interrogate a secondary material for said flaw, the improvement to said method comprising the steps of:

providing a first solid structure for originally receiving said interrogating ultrasound wave packet;

providing a second solid structure separated from said first structure by a gap;

providing a gas in said gap;

transmitting an interrogating wave packet of ultrasound to said first structure:

changing said wave packets in frequency to determine when said wave packet contains a frequency which when traveling through gas such as that gas flooding said gap includes an instantaneous standing path length within the gas which is at least twice the dimension of the gap to be bridged, said interrogating wave packet of said ultrasound containing said determined frequency having a wavelength relative to the gas in said gap to create at least one constructively interfering standing wave node between said first solid structure and said second solid structure within said gas flooding said gap, whereby ultrasound of said frequency passes across said gap;

passing said ultrasound of said determined frequency into said second solid structure to acoustically interrogate the second solid structure for flaws;

providing a receiving transducer;

receiving reflected ultrasound from the interrogated second solid structure across said gap at the constructively interfering standing wave, through the first solid structure and then to said transducer for receipt and analysis of the received ultrasound.

12. The invention of claim 11 and wherein said provided receiving transducer transmits said interrogating wave packet.

13. Apparatus for the nondestructive acoustical inspection including the ultrasonic inspection of materials through barriers such as gaps in manufactured parts between first and second solid structures wherein ultrasound passes through a first solid structure, across said gap and to interrogate a second solid structure for said flaw, the improvement comprising:

means for providing a medium having a predictable speed of ultrasound in said gap;

means for transmitting an ultrasound wave packet to said first solid structure, the ultrasound of said wave packet when traveling through medium such as that medium flooding said gap including an instantaneous standing path length within the medium which is at least twice the dimension of the gap to be bridged, said interrogating wave packet of said ultrasound containing a frequency having a wavelength relative to the medium in said gap to create at least one constructively interfering standing wave node between said first solid structure and said second solid structure within said medium flooding said gap, whereby ultrasound of said frequency passes across said gap;

a receiving transducer for receiving reflected ultrasound from said transducer whereby the acoustical signal from said interrogated second solid structure across said gap at the constructively interfering standing wave, through the first solid structure and then to said transducer for receipt and analysis of the received ultrasound for flaws in said second solid structure.

14. The apparatus of claim 13 and wherein said means for providing a medium within said gap includes means for providing a gas for displacing ambient gas in said gap.

15. The apparatus of claim 14 and wherein said provided gas comprises helium.

16. The apparatus of claim 14 and wherein said means for transmitting includes an electrically actuated ultrasound transducer, said transducer communicated to a couplant fluid between said transducer and said first material.

* * * * *